United States Patent
Waxman

(10) Patent No.: US 7,297,148 B2
(45) Date of Patent: Nov. 20, 2007

(54) SURGICAL SAFETY PROCEDURE AND APPARATUS

(76) Inventor: Bruce Waxman, 4398 Hickory Dr., Palm Beach Gardens, FL (US) 33418

( * ) Notice: Subject to any disclaimer, the term of this patent is extended or adjusted under 35 U.S.C. 154(b) by 986 days.

(21) Appl. No.: 10/446,007

(22) Filed: May 22, 2003

(65) Prior Publication Data

US 2004/0236871 A1    Nov. 25, 2004

(51) Int. Cl.
*A61B 17/00* (2006.01)
*G06F 17/60* (2006.01)
(52) U.S. Cl. .......................................... 606/130; 710/1
(58) Field of Classification Search .................. 606/1; 710/1–2
See application file for complete search history.

(56) References Cited

U.S. PATENT DOCUMENTS

| | | | |
|---|---|---|---|
| 4,333,072 A | 6/1982 | Beigel | |
| 4,682,415 A | 7/1987 | Adell | |
| 4,973,944 A | 11/1990 | Maletta | |
| 5,115,223 A | 5/1992 | Moody | |
| 5,493,805 A | 2/1996 | Penuela et al. | |
| 5,609,716 A | 3/1997 | Mosher, Jr. | |
| 5,615,504 A | 4/1997 | Peterson et al. | |
| 5,646,592 A | 7/1997 | Tuttle | |
| 5,781,110 A | 7/1998 | Habeger, Jr. et al. | |
| 5,973,598 A | 10/1999 | Beigel | |
| 5,973,600 A | 10/1999 | Mosher | |
| 6,099,522 A * | 8/2000 | Knopp et al. ................. 606/10 |
| 6,181,287 B1 | 1/2001 | Beigel | |
| 6,414,543 B1 | 7/2002 | Beigel et al. | |
| 6,642,782 B2 | 11/2003 | Beigel et al. | |
| 6,888,502 B2 | 5/2005 | Beigel et al. | |
| 2003/0101077 A1 | 5/2003 | Wohl | |

* cited by examiner

*Primary Examiner*—Vy Bui
(74) *Attorney, Agent, or Firm*—McHale & Slavin, P.A.

(57) ABSTRACT

A safety device and procedure for use in correlating a patient and an intended surgical procedure uses a micro-chip programmed with specific information about the patient and the surgery. Part of the information lists an authorized person that may remove the micro-chip. The micro-chip is attached to the patient at the anatomical location of the intended surgery. The chip is scanned to retrieve the information before surgery and if the patient and the surgery are correlated, a printout is placed in the patient's chart. The authorized person removes the chip and surgery proceeds.

1 Claim, 2 Drawing Sheets

SURGICAL SAFETY PROCEDURE AND APPARATUS

FIELD OF THE INVENTION

This invention relates to the field of safety devices and procedures for ensuring that proper surgical procedures are performed on the proper patient.

BACKGROUND OF THE INVENTION

There have been notorious stories involving patients who have undergone erroneous surgical procedures, including amputation and removal of organs. In some instances, the amputation involved the wrong part of the right patient. In other instances, the surgery involved a patient who was not even scheduled for the surgery performed. Unfortunately, the errors giving rise to these stories do occur.

The use of identification bracelets is a method of tracking patients, their conditions, and contraindications. After the bracelets are put on, they have to be cut off. This prevents lost or misplaced bracelets. The bracelets, usually, cannot be placed near the surgical site.

Some hospitals, clinics and doctors now use ad hoc procedures to eliminate such terrible mistakes. In some instances, the medical personnel responsible for preparing patients for surgery will use a marker to denote a surgical site. An approved system is directed to surgeons and is titled, Sign Your Site, which requires the surgeon to mark the surgical site. These markings have some drawbacks because a mark that is not physically close to an incision may be totally covered by surgical draping before the operation; the surgeon may not be present to sign his site until the patient is draped which would result in disturbing the sterile surgical field.

Attempts to diminish the incidence of these errors have been made such as writing "no" on the incorrect extremity or "yes" on the correct extremity, requiring the surgeon to sign the intended incision site, and requiring the surgeon to read the operative consent in addition to personally identifying the patient, etc. These have all helped, but the problem persists.

The American Academy of Orthopaedic Surgeons has undertaken a voluntary campaign to have the surgeon sign the incision site; surgeons in Canada have tried the same approach the result so far has been encouraging, but not yet satisfactory. A recently published study which attempted to enlist the patient to assist in the prevention of wrong-site surgery by signing "yes" in the area he/she expects the incision to be made was a failure due to lack of compliance. The Joint Commission on Accreditation of Healthcare Organizations has wisely required a "time out" prior to starting surgery during which the patient is identified, the "yes" over the incision site is reviewed, and the surgical consent is read. Occasionally, however, the surgical team forgets to take the "time out" or remembers to do it only after the surgery has begun. Also, the "time out" frequently occurs while the surgeon is prepping and draping the operative site—his/her attention may be diverted by the prepping procedure despite the best intentions.

Another source of confusion is that after a thorough review of all the proper information, the patient is occasionally turned over or around (in some instances, while the surgeon is out of the operating room to scrub or check instruments)—right and left are then reversed, and if the change in position is forgotten or unexpected, the incorrect side may be operated upon.

Some safety procedures have attempted to involve the patient in the prevention of wrong-site surgery. In The Journal of Bone & Joint Surgery, Vol. 85-A, No. 5, May 2003, a study of such a procedure was published. The over-all conclusion was that patients were not very responsive to following explicit preoperative instructions to place an indicator, such as YES on one part of the body and NO on a similar part. As mentioned above, some patient marks were not close enough to the site to be useful and some were missing entirely. It seems that the patient becomes too passive in the medical environment and assumes that these details will be correctly executed.

In the computer industry, certain tracking systems employ a micro-chip with a programmable memory that can be subsequently read by a scanner. Such micro-chips are manufactured by Texas Instruments under the name, Tag It Smart Label or TI-RFid. The micro-chip may be incorporated into a "smart card" and may be read by a wireless reader integrated with a PC (personal computer), PDA (personal digital assistant) and/or printer. The tags and readers operate in the 13.56 MHZ range. The chips are used in facility protection and admittance along with asset tracking.

Another computer product is called iButton, by Dallas Semiconductor MAXIM, that has a programmable memory chip in a 16 mm stainless steel disk that may be hosted by a PC, PDA or laptop computer. The disk has an annular flange that serves as the attachment structure. The iButton has a 1-wire reader to transfer data from the chip to a computer. It is also used for admittance, asset tracking and authentication.

The chips in either of these products are capable of storing and retrieving more than enough information to satisfy the needs of medical personnel to correlate a patient with a condition and a surgical procedure to be performed.

What is needed in the art is a safety apparatus that can be programmed with essential information about the patient, the surgical procedure to be performed, and designate a person with responsibility for insuring the programmed information is correct. Accompanying procedure includes the steps of applying the apparatus to the patient, confirming the programming and the site to be corrected, and removing the apparatus.

SUMMARY OF THE PRESENT INVENTION

Disclosed is a safety device and procedure for use in correlating a patient and an intended surgical procedure. The safety device uses a micro-chip programmed with specific information about the patient and the surgery. Included in the information are instructions regarding the authorized person that may remove the micro-chip. The micro-chip is attached to the patient at the anatomical location of the intended surgery. The chip is scanned to retrieve the information before surgery and surgery may proceed if the information correlates. A printout may be placed in the patient's chart. Only the authorized person can remove the chip before the surgery proceeds.

Accordingly, an objective of this invention is to teach the use of a micro-chip programmed with specific retrievable medical information that is attached to a patient at the intended surgical site to store information unique to the patient and the surgical procedure.

Another objective of this invention is to teach the use of a procedure that designates a particular individual to validate the programmed information, the placement of the micro-chip and its removal from the patient.

A further objective of this invention is to teach the production and use of a written record of the patient and surgical procedure.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
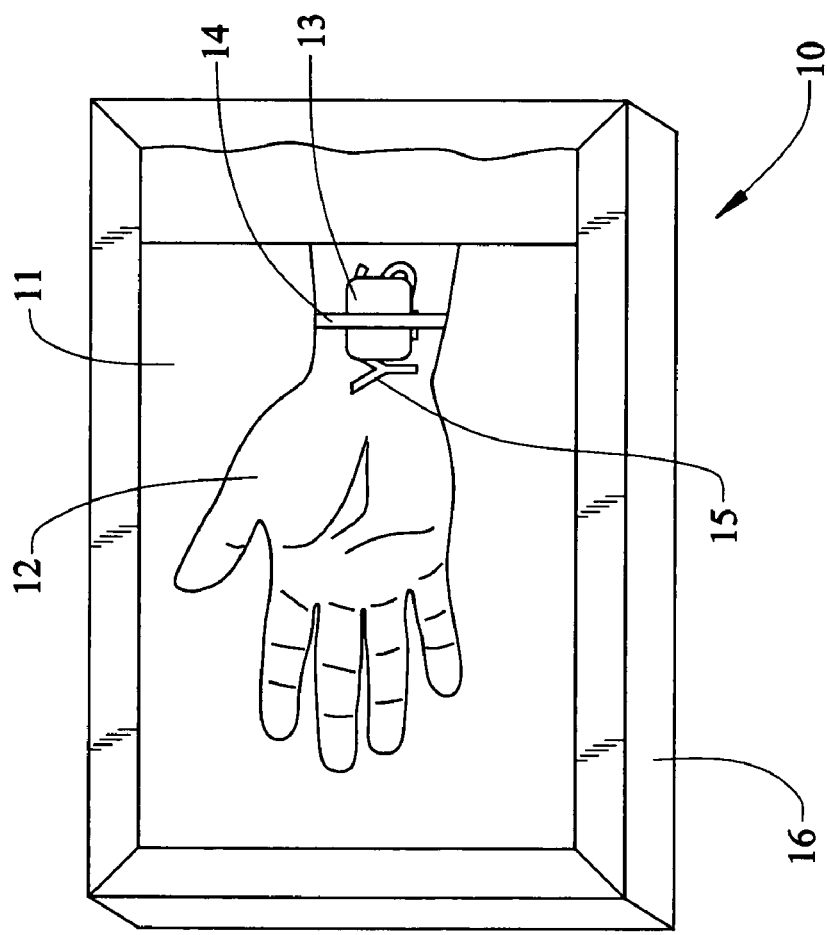
FIG. 1 is a top view of an operating field.
Figure 2:
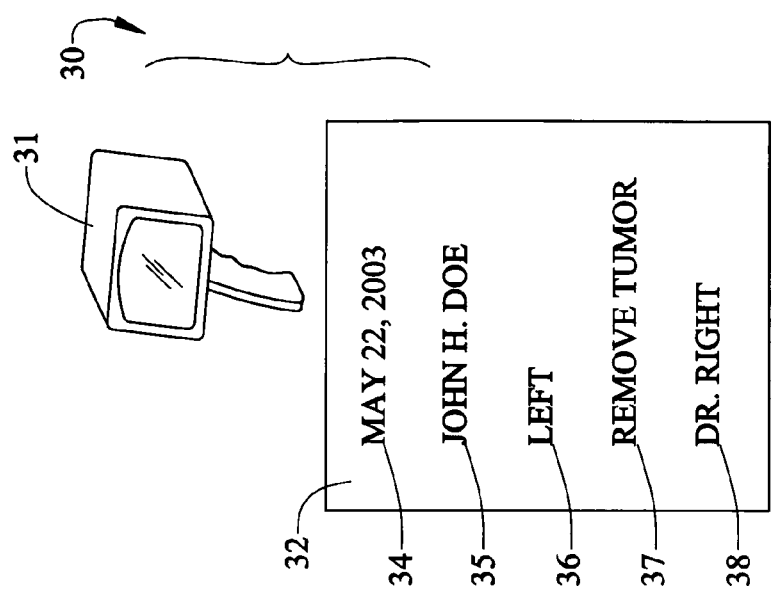
FIG. 2 is a diagrammatic view of the chip and host of this invention.
Figure 3:
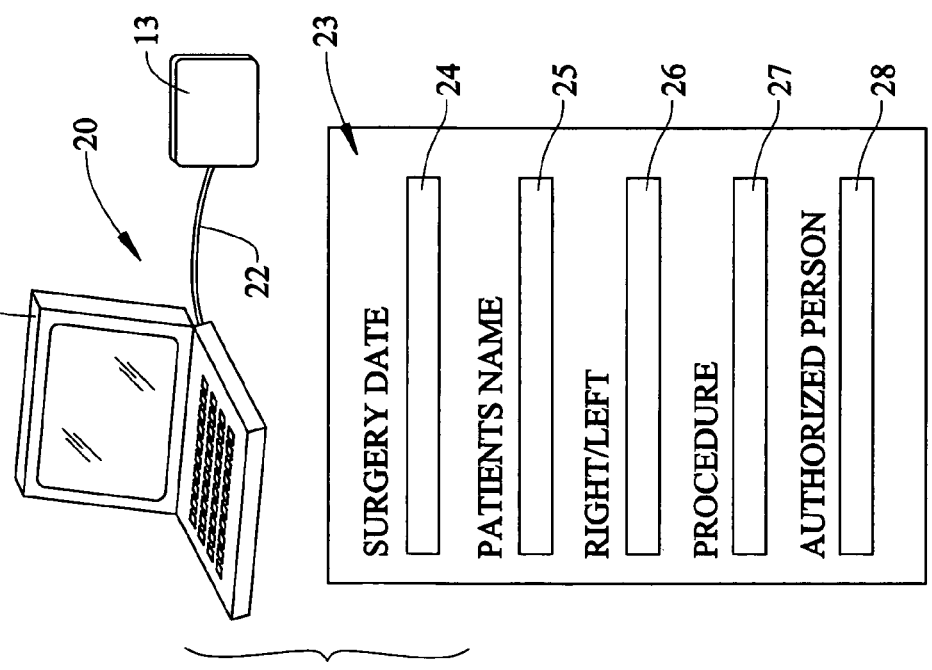
FIG. 3 is a diagrammatic view of the reading of the chip of this invention.

The micro-chip of this invention is programmed to store specific information concerning a particular patient and a particular surgery. The computer chip is either attached to the patient or the patient's medical chart to accompany the patient during procedures conducted in the medical care facility. As shown in FIG. 1, the safety apparatus 10 is shown in the operating room. A patient's left hand 12 is shown on an operating table in the operative field 11 before final prepping. The surgical drapes 16 frame the operative field. The computer chip 13 is attached to the patient by most any means, such as adhesive tape 14, on the site of the intended surgical procedure. A "YES" marking 15 has also been applied to the patient's skin at the specific site of the intended surgery. The mark may be made by the patient or hospital personnel.

The safety procedure that incorporates the micro-chip begins with a decision by and between the doctor and the patient to follow a certain treatment protocol. In the instance shown here, the patient has a tumor in the left wrist and the treatment is to remove the tumor surgically. In the preoperative visit or in the holding area prior to surgery a micro-chip is programmed with the following information: a) the date of the surgery 24; b) full name of the patient 25; c) the area of the surgery, right, left or bilateral 26; d) the surgical procedure to be accomplished 27; and e) the name of the person authorized to remove the micro-chip 28. This programming may be accomplished by a computer host 21 through a wire 22 or wireless connection to the micro-chip 13. As shown, the application uses a text box to load the information.

If the chip is programmed during a preoperative visit, the chip may be attached to the patient's chart for placement at a later date or immediately before surgery. In some cases, the chip may be programmed in the doctor's office and may be brought to the surgical facility by the patient.

With regard to the location of the surgery, a bilateral procedure(s) is treated as separate procedures and requires the use of two micro-chips. This permits each chip to be located at the site of the intended surgery.

The authorized person to remove the micro-chip from the patient is preferably the surgeon or a certified physician's assistant, or may be another entrusted person such as a resident or nurse. The important point is that only that person is supposed to remove the chip from the surgical site. There is some flexibility in that the patient's own doctor or the surgeon performing the operation may order the chip removed in the absence of the authorized person.

In the holding area, immediately before surgery, the micro-chip 13 is scanned by scanner 31. The information is retrieved by medical personnel and reviewed with the patient to confirm that the information is correct.

Preliminary prepping of the surgical site is then performed, including washing, shaving, and or disinfecting, if indicated. A sterile marker may be used to write on the operative site, the word, "YES." The micro-chip is then attached to the patient, for example the use of adhesive tape 14, is shown. Other devices, such as adhesive spray, tethers, etc., may be used to attach the micro-chip depending on the surgical site. The surgical site is not to be disturbed by an incision of any kind, at this time.

The patient is now ready to be taken into the operating room. A sedative may be administered at this time. In the operating room, the patient may be anesthetized and placed in the final position for surgery. The micro-chip is scanned with a hand held scanner 31 operated by the surgeon or other designated operating personnel or authorized by the information on the micro-chip. All the information is reviewed by the operating room personnel and the authorized agent. The retrieved information includes; a) the date 34; b) the patient's name 35; c) the location 36; d) the procedure 37; and e) the authorized person to remove the chip 38. If any discrepancy is noted between the information and the physical location of the micro-chip and/or marker or the named patient on the table, the issue may be resolved by the surgeon or the surgery is canceled.

A printout of this information may be produced by the hosting device. The printout is then signed by the authorized person who removes the micro-chip from the patient. The printout is maintained with the patient's chart. The micro-chip may then be discarded. Alternatively, a voice synthesizer can be used wherein information is retrieved and an audible reproduction produced.

Once the micro-chip has been removed, the position of the patient may not be changed unless by direct order of the surgeon or the authorized person. At this time, the final sterile preparation is completed and the surgery can begin.

By way of example, in a doctor's office, or during a preoperative visit, a small computer chip is programmed with the following critical information: the date of surgery, full name (first name first, to avoid confusion), right or left (if applicable), the name of the operation to be performed, and the name of the surgeon and -his/her physician's assistant or surgical resident who is authorized to start the operation. A reader then scans the chip; the nurse and the patient review the information to be sure it is correct.

On the day of the surgery, the chip is again scanned and the information is reviewed by the patient. If correct, either the nurse or the patient, while the patient is wide awake, stick the chip on the skin where the incision is to be made (If allergic to adhesive, hypoallergenic tape may be used.) This helps assure the chip is placed over the proper site. Since the patient assisted in programming and placing the chip, the chance of error is diminished. The chip is left in place during transport to the operating room, while an anesthetic is administered and while the patient is placed in the final position for surgery. This method diminishes the chance that the information regarding identity and surgery will accidently be switched with that of another patient as it may when the information is contained in a separate hospital chart. It also helps prevent mistaking left for right if the patient is turned face down instead of face up.

The chip is then scanned by the surgeon or P.A.-C./surgical resident who the patient previously approved, and the information is reviewed. In this way the surgeon does not have to rely on recognizing the patient with a cap over the hair, a tube in the throat, no make-up, no dentures, etc. He/She is the most highly trained, responsible person in the operating room to do this final check. It is much preferable to having a nurse read the operative consent from a chart and the nurse, or possibly another person, read the name from a wrist band—while very competent, these personnel are not the most qualified in the OR at the time. Also, there is a remote possibility that the operative consent may be that of another patient.

Since all the pertinent information is in one location (the chip), and because it has not physically been apart from the body, it is unlikely that it will inadvertently be, switched with that of another patient. Furthermore, while looking at the reader, the surgeon is forced to focus his/her attention on the task of confirming the name, the procedure, etc. Using SURGICHIP your surgeon is less likely to forget the review of information since the chip would then remain in place as a physical barrier to the incision.

After the information on the chip is confirmed to be correct, the surgeon or P.A.-C./resident removes the chip- no other person is permitted to do it. The chip is not scanned by a nurse, tech, or anyone less responsible than the surgeon or his/her approved assistant. This also assures that the person appointed to do the surgery will be physically present in the operating room when the surgery begins rather than on his/her way, in a meeting, in the dressing room, etc.

Once the chip has been removed, the position-may not be changed. This diminishes the chance that the position will be altered, unnoticed by the surgeon, in a way that right would appear to be left, etc. (such as being turned over or around)

Since the word "yes" is also written on the incision site according to the usual recommended method, and remains intact during the final surgical prep, an identifying mark is still present after the chip has been removed A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

What is claimed is:

1. A safety procedure for correlating patients with the intended surgical procedure comprising the steps of;
    a) programming a micro-chip with specific information concerning a particular patient including his name; the date of the intended surgery, the anatomical location of the surgery, the particular surgical procedure, and the name of an authorized person to remove said micro-chip,
    b) scanning said micro-chip to retrieve said information and reviewing said information with the patient,
    c) attaching said micro-chip to said patient at said anatomical site of said surgery;
    d) moving said patient to an operating room,
    e) scanning said attached micro-chip and retrieving said information,
    f) confirming with said authorized person that the patient and the surgical procedure are correlated and the anatomical location of said micro-chip is correct,
    g) producing a printout of said information,
    h) said authorized person removing said micro-chip, and
    i) proceeding with said surgery at said anatomical location.

* * * * *